US00PP25031P3

(12) United States Plant Patent
Suphachadiwong

(10) Patent No.: US PP25,031 P3
(45) Date of Patent: Nov. 4, 2014

(54) ***PHALAENOPSIS* PLANT NAMED 'SUPHAL1307'**

(50) Latin Name: ***Phalaenopsis* hybrid**
Varietal Denomination: SUPHAL1307

(71) Applicant: Thumrong Suphachadiwong, Chonburi (TH)

(72) Inventor: Thumrong Suphachadiwong, Chonburi (TH)

(73) Assignee: Suphalchatawong Innovation (TH)

( * ) Notice: Subject to any disclaimer, the term of this patent is extended or adjusted under 35 U.S.C. 154(b) by 35 days.

(21) Appl. No.: 13/815,778

(22) Filed: Mar. 15, 2013

(65) Prior Publication Data

US 2014/0283256 P1 Sep. 18, 2014

(51) Int. Cl.
*A01H 5/00* (2006.01)

(52) U.S. Cl.
USPC ..... Plt./311

(58) Field of Classification Search
USPC ..... Plt./311
See application file for complete search history.

*Primary Examiner* — Kent L Bell
(74) *Attorney, Agent, or Firm* — Cassandra Bright

(57) ABSTRACT

A new and distinct *Phalaenopsis* cultivar named 'SUPHAL1307' is disclosed, characterized by short plant height, small leaves, small white flowers with purple blush at base as well as white lip with yellow and purple spots. The new variety is a *Phalaenopsis*, typically produced as an indoor ornamental plant.

2 Drawing Sheets

Figure 1:
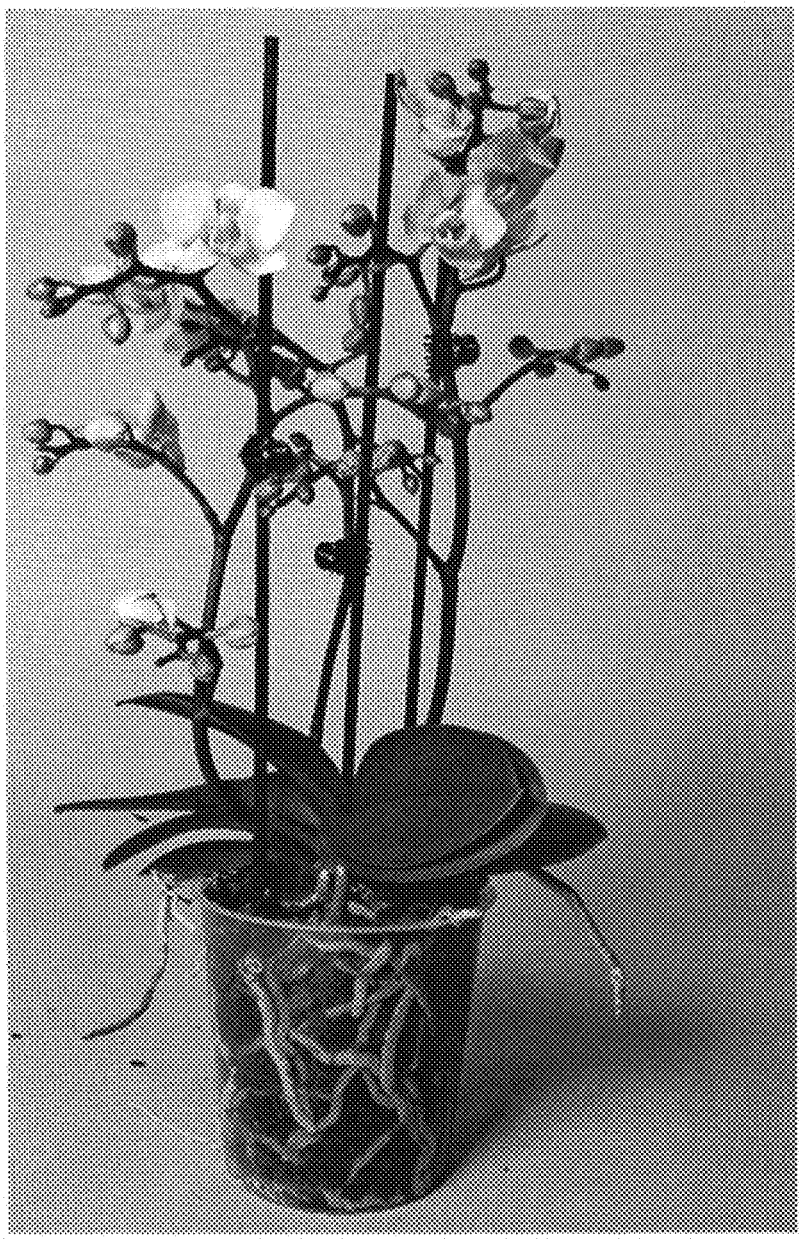

Latin name of the genus and species: *Phalaenopsis* hybrid. Variety denomination: 'SUPHAL1307'.

BACKGROUND OF THE INVENTION

This application relates to a new cultivar of *Phalaenopsis* hybrid. The new variety is the product of a planned breeding program. The new variety originated as a seedling from the crossing of the unpatented, proprietary seed parent *Phalaenopsis* 'TP174' with the unpatented, proprietary pollen parent referred to as *Phalaenopsis* 'BTXS6'. The crossing was made by the inventor in his research greenhouse in Chonburi, Thailand in January of 2006.

The new variety was first selected by the inventor, Thumrong Suphachadiwong, a citizen of Thailand, in January of 2009 in a research greenhouse belonging to the inventor in Chonburi, Thailand. After identifying the new variety as a potentially interesting selection, the inventor continued confidential testing and propagation of 'SUPHAL1307', assessing stability of the unique characteristics of this variety.

Asexual reproduction of the new cultivar 'SUPHAL1307' was first performed at a commercial laboratory belonging to the inventor in Chonburi, Thailand by tissue culture in February of 2009. Access to all plants was restricted, as plants were kept in a greenhouse not open to the public, and tissue culture plantlets were in a laboratory belonging to the inventor, and not accessible to the public. Through subsequent propagation, multiple generations have been reproduced, which have shown that the unique features of this cultivar are stable and reproduced true to type.

SUMMARY OF THE INVENTION

The cultivar 'SUPHAL1307' has not been observed under all possible environmental conditions. The phenotype may vary somewhat with variations in environment such as temperature, day length, and light intensity, without, however, any variance in genotype.

The following traits have been repeatedly observed and are determined to be the unique characteristics of 'SUPHAL1307'. These characteristics in combination distinguish 'SUPHAL1307' as a new and distinct *Phalaenopsis* cultivar:

1. Short plant height.
2. Small leaves.
3. Small white flowers with purple base.
4. White lip with yellow and purple spots.

PARENT COMPARISON

Plants of the new cultivar 'SUPHAL1307' are similar to the seed parent, *Phalaenopsis* 'TB174' in most horticultural characteristics. The new variety, however, produces a more compact plant than the seed parent. Additionally, the new variety produces smaller flowers than the seed parent.

Plants of the new cultivar 'SUPHAL1307' are similar to the pollen parent, Phalaenopsis 'BTXS6' in most horticultural characteristics. Plants of the new variety however produce larger flowers with more white than the pollen parent.

COMMERCIAL COMPARISON

'SUPHAL1307' is similar to the unpatented commercial variety *Phalaenopsis* 'Fragrance' in most horticultural characteristics. However the new variety, 'SUPHAL1307' differs from 'Fragrance' in the following characteristics:

1. Apical lobe is different shape.
2. Leaves are narrower.
3. Smaller flowers.
4. Apical and lateral lobes have larger dark purple spots.

'SUPHAL1307' is similar in most horticultural characteristics to the unpatented commercial variety *Phalaenopsis*

'Amaglad' in most horticultural characteristics. However the new variety, 'SUPHAL1307' differs from 'Amaglad' in the following characteristics:

1. Apical lobe is different shape.
2. Leaves are narrower.
3. Smaller flowers.
4. Apical and lateral lobes have much more purple, but much less yellow coloration.
5. Plant height is shorter.
6. Petals more open.
7. Darker purple blush in the petals and sepals.

BRIEF DESCRIPTION OF THE PHOTOGRAPH

The accompanying photographs in FIG. 1 illustrates in full color a typical plant of 'SUPHAL1307' grown in a commercial greenhouse in Zuidbroek, the Netherlands. This plant is approximately 18 months old after deflasking, shown planted in an 11 cm container.

Figure 2:
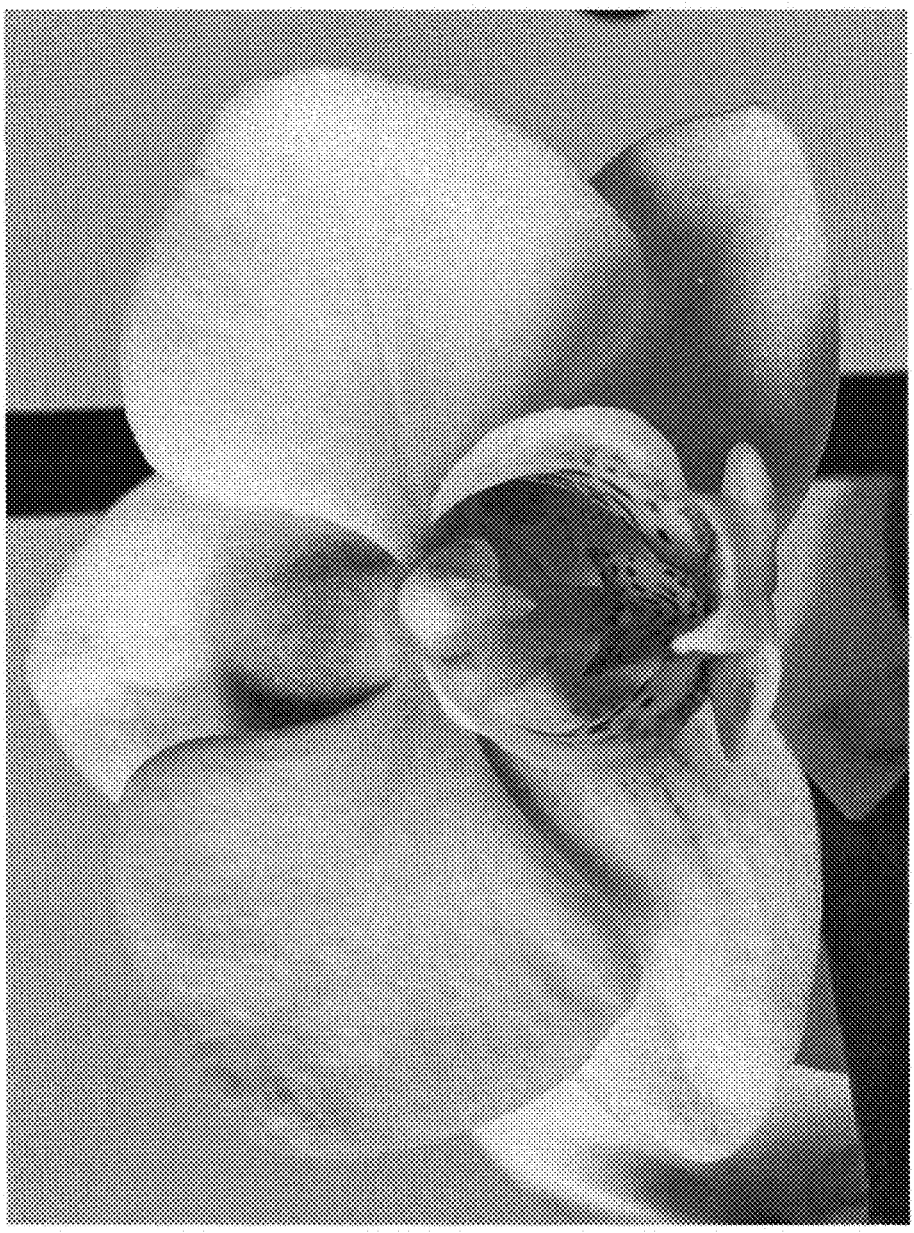

FIG. 2 illustrates a close up of the individual flower. The photographs were taken using conventional techniques and although colors may appear different from actual colors due to light reflectance it is as accurate as possible by conventional photographic techniques.

DETAILED BOTANICAL DESCRIPTION

In the following description, color references are made to The Royal Horticultural Society Colour Chart 2007, except where general terms of ordinary dictionary significance are used. The following observations and measurements describe 'SUPHAL1307' plants grown in a commercial greenhouse in Zuidbroek, the Netherlands. This plant is approximately 18 months old after deflasking, shown planted in an 11 cm container. Temperatures ranged between 18° C. and 28° C. day and night. No photoperiodic or chemical treatments were given to the plants. During bright Summer conditions, shade was given. During dark Winter months, supplemental light was given at unspecified amounts. Measurements and numerical values represent averages of typical plant types.

Botanical classification: *Phalaenopsis* hybrid 'SUPHAL1307'.

PROPAGATION

Type of propagation typically used: Tissue culture.

Time to initiate roots: About 21 days at approximately 28° C.

Time to produce a rooted cutting/liner: About 26 weeks at approximately 18° C. to 28° C.

Root description: Thick (typical for *Phalaenopsis*) and rounded, average diameter: 5 mm, colored greyed-green; near RHS 190A.

PLANT

Growth habit: Monopodial.

Height from to of soil line top top of foliage: Average 5.9 cm.

Height from to of soil line top top of flowers: Average 29.5 cm.

Plant spread: At widest, average: 22.3 cm; at narrowest: 17.6 cm.

Normal pot size: 11 cm.

Growth rate: Moderate.

Number of leaves per plant: Average 8.

FOLIAGE

Leaf:

*Arrangement*.—Distichous.

*Average length*.—Approximately 11.1 cm (including sheath).

*Average width*.—Approximately 5.2 cm.

*Shape of blade*.—Obovate.

*Aspect*.—Horizontal.

*Apex*.—Unequal acute.

*Base*.—Cuneate. Sheath length: Average 1.0 cm. Sheath width: Average 1.4 cm. Sheath color: Green; near RHS 143C.

*Margin*.—Entire.

*Texture of top surface*.—Smooth, very slightly furrowed.

*Texture of bottom surface*.—Smooth.

*Appearance*.—Glossy on both surfaces.

*Color*.—Young foliage upper side: Green; near RHS N137B. Young foliage under side: Yellow-green; near RHS 146A to 146B, dark green near the margins; near RHS N137B. Mature foliage upper side: Green; near RHS N137B. Mature foliage under side: Yellow-green; near RHS 146A to 146B, dark green near the margins; near RHS N137B.

*Venation*.—Type: Camptodromous. Venation coloration: Upper side green; near RHS N137B, under side yellow-green; near RHS 146A to 146B, main vein on under side green; near RHS N137A to N137B.

Petiole: No petiole present.

FLOWERING CHARACTERISTICS

Flower bud:

*Rate of opening*.—Approximately 3 days after stage described.

*Length*.—Approximately 1.4 cm.

*Diameter*.—Approximately 1.1 cm wide and 1.3 cm high.

*Shape*.—Broad ovate.

*Color*.—Yellow-green; near RHS 145B, lighter on upper side; near RHS 150C.

Peduncle:

*Length*.—Approximately 27.7 cm.

*Width*.—Approximately 0.4 cm.

*Aspect*.—Approximately 65° angle to rosette.

*Strength*.—Strong.

*Texture*.—Smooth.

*Appearance*.—Matte.

*Color*.—Green; near RHS 143B to 143C, finely dotted yellow-green; near RHS 145C.

Inflorescence:

*Flowers per stem*.—Average 23.

*Inflorescence arrangement*.—Compound panicle.

*Inflorescence height*.—Approximately 14.6 cm (measured from lowest branching of panicle to top of inflorescence).

*Inflorescence width*.—Approximately 15.9 cm.

Individual flowers:

*Flower type*.—Single zygomorphic flower.

*Shape*.—Rounded deltate.

*Length* (*height*).—Approximately 3.9 cm.

*Width*.—Approximately 4.7 cm.

*Depth*.—Approximately 2.6 cm.
*Fragrance*.—No fragrance.
*Persistent*.—Non-persistent.
*Quantity of petals*.—2 true petals.

Petals:
*Arrangement*.—One petal on each side of the column.
*Length*.—Approximately 2.2 cm.
*Width*.—Approximately 2.4 cm.
*Shape*.—Deltoid to short rhomboidal.
*Apex*.—Obtuse.
*Base*.—Cuneate.
*Margin*.—Entire.
*Texture*.—Upper (forward) surface: Smooth, moderately velvety.
*Texture*.—Lower (back) surface: Smooth, moderately velvety.
*Appearance*.—Matte both surfaces.
*Color*.—When opening, forward surface: White; near RHS NN155D, base purple; near RHS 76A. When opening, back surface: White; near RHS NN155D, base purple; near RHS 76B and 76C. Fully Opened, forward surface: White; near RHS NN155D, base purple; near RHS 76A. Fully Opened, back surface: White; near RHS NN155D, base purple; near RHS 76B to 76C. Fading, forward surface: Not fading, only becoming non- velvety. Fading, back surface: Not fading, only becoming non- velvety.
*Color venation*.—Fully Opened, forward surface: White; near RHS NN155D, base purple; near RHS 76A. Fully Opened, back surface: White; near RHS NN155D, base purple; near RHS 76B and 76C.

Labellum:
*Shape*.—Three-parted.
*Length*.—Approximately 1.6 cm.
*Width*.—Approximately 1.3 cm.
*Texture*.—Smooth, slightly velvety.
*Appearance*.—Matte.
*Tip*.—Cleft, tips cirrhose, curled upward.
*Base*.—Cuneate.
*Color*.—When opening, forward surface: Central lobe white; near RHS NN155D, base yellow; near RHS 12C, lateral lobes purple; near RHS 76B, dotted red-purple; near RHS 71B, margins white; near RHS NN155D, lower margin tinged yellow-orange; 14C, callosities yellow; near RHS 6C, dotted red-purple; near RHS 61A. When opening, back surface: Central lobe white; near RHS NN155D, margins near the base yellow; near RHS 12D, lateral lobes purple; near RHS 76C, margins white; near RHS NN155D, lower margin tinged yellow-orange; 14C. Fully Opened, forward surface: Central lobe white; near RHS NN155D, base yellow; near RHS 12C, lateral lobes purple; near RHS 76B, dotted red-purple; near RHS 71B, margins white; near RHS NN155D, lower margin tinged yellow-orange; 14C, callosities yellow; near RHS 6C, dotted red- purple; near RHS 61A. Fully Opened, back surface: Central lobe white; near RHS NN155C to NN155D, margins near the base yellow; near RHS 12D, lateral lobes purple; near RHS 76C, margins white; near RHS NN155D, lower margin tinged yellow-orange; 14C. Fading, forward surface: Not fading, only becoming non-velvety. Fading, back surface: Not fading, only becoming non-velvety.
*Color venation*.—Fully Opened, forward surface: Main vein of central lobe red; near RHS 42B, margined orange; near RHS 26C, no other venation visible. Fully Opened, back surface: Main vein of central lobe red; near RHS 50D, no other venation visible.
*Margin*.—Entire.

Sepals:
*Quantity*.—3.
*Texture*.—Smooth, moderately velvety.
*Appearance*.—Matte.
*Length*.—Approximately 2.2 cm.
*Width*.—Dorsal sepal approximately 1.8 cm. Lateral sepals approximately 1.5 cm.
*Shape*.—Ovate.
*Apex*.—Broad bluntly acute.
*Base*.—Broad cuneate.
*Margin*.—Entire.
*Color*.—
*Fully opened, forward surface*.—White; near RHS NN155C to NN155D, base red-purple; near RHS N74D, lateral sepals finely dotted red-purple at the base; near RHS 64A.
*Fully opened, back surface*.—Purple; near RHS 75C to 75D, margins white; near RHS NN155C to NN155D.

Pedicels:
*Length*.—Approximately 2.2 cm.
*Diameter*.—Approximately 0.3 cm.
*Angle*.—Approximately 80° to peduncle.
*Strength*.—Moderately strong.
*Texture*.—Smooth.
*Appearance*.—Moderately glossy.
*Color*.—Green; near RHS 143A, distal part yellow-green and green-white; near RHS 145D and 157A.

REPRODUCTIVE ORGANS

*Stamens, style and stigma fused into column*?.—Yes.
*Column length*.—Approximately 0.8 cm.
*Column diameter*.—Approximately 0.5 cm.
*Column color*.—Purple; near RHS 75A.
*Ovary*.—Position: Inferior. Diameter: Approximately 0.3 cm. Color: Purple; near RHS 76D.
*Pollen color*.—Yellow-orange; near RHS 23A.

OTHER CHARACTERISTICS

Disease resistance: Neither resistance nor susceptibility to the normal diseases found in *Phalaenopsis* has been observed.
Drought tolerance and cold tolerance: Normal for species.
Fruit/seed production: No fruits/seeds detected to date.

What is claimed is:

1. A new and distinct cultivar of *Phalaenopsis* plant named 'SUPHAL1307' as herein illustrated and described.

* * * * *